(12) United States Patent
Bauer et al.

(10) Patent No.: US 10,165,935 B2
(45) Date of Patent: Jan. 1, 2019

(54) MEASURING HEAD OF AN ENDOSCOPIC DEVICE AND PROCESS FOR INSPECTING AND MEASURING AN OBJECT

(71) Applicant: Rolls-Royce Deutschland Ltd & Co KG, Blankenfelde-Mahlow (DE)

(72) Inventors: Joachim Bauer, Berlin (DE); Sigurd Schrader, Berlin (DE); Martin Burger, Wildau (DE); Silvio Pulwer, Berlin (DE); Friedhelm Heinrich, Berlin (DE); Viachaslau Ksianzou, Berlin (DE); Patrick Steglich, Berlin (DE); Jean Blondeau, Berlin (DE); Claus Villringer, Berlin (DE)

(73) Assignee: Rolls-Royce Deutschland Ltd & Co KG, Blankenfelde-Mahlow (DE)

( * ) Notice: Subject to any disclaimer, the term of this patent is extended or adjusted under 35 U.S.C. 154(b) by 0 days.

(21) Appl. No.: 15/007,447

(22) Filed: Jan. 27, 2016

(65) Prior Publication Data
US 2016/0220104 A1   Aug. 4, 2016

(30) Foreign Application Priority Data
Jan. 29, 2015   (DE) .................. 10 2015 201 561

(51) Int. Cl.
*G01N 21/00*   (2006.01)
*A61B 1/06*    (2006.01)
(Continued)

(52) U.S. Cl.
CPC .......... *A61B 1/0661* (2013.01); *A61B 1/0646* (2013.01); *G01B 11/2513* (2013.01);
(Continued)

(58) Field of Classification Search
CPC .. A61B 1/0646; A61B 1/0661; G01N 21/954; G01N 2021/9544; G01B 11/2518
(Continued)

(56) References Cited

U.S. PATENT DOCUMENTS 5,047,847 A * 9/1991 Toda ................. A61B 1/05
                                                    348/345
5,068,679 A    11/1991 Kikuchi
(Continued)

FOREIGN PATENT DOCUMENTS

DE        19803679 A1    8/1999
DE    102007005388 A1    8/2008
(Continued)

OTHER PUBLICATIONS

Modrow, Daniel; Echtzeitfähige aktive Stereoskopie für technische und biometrische Anwendungen (Real-time active stereoscopy for technical and biometric applications); Dissertation, Jun. 17, 2008 TU; München (English translation of abstract).
(Continued)

*Primary Examiner* — Isiaka Akanbi
(74) *Attorney, Agent, or Firm* — Shuttleworth & Ingersoll, PLC; Timothy Klima

(57) ABSTRACT

A measuring head of an endoscopic device is provided. The measuring head has an optical projection unit (projection optics) intended and designed to illuminate an object to be examined with light, and an optical measurement unit (measurement optics) intended and designed to record the light reflected or diffused from the object to be examined. It is provided that the optical measurement unit (measurement optics) has an aperture diaphragm of which the aperture is settable.

22 Claims, 8 Drawing Sheets

(51) Int. Cl.
  *G02B 23/24* (2006.01)
  *G01N 21/954* (2006.01)
  *G01B 11/25* (2006.01)
  *G02B 5/00* (2006.01)

(52) U.S. Cl.
  CPC ....... *G01B 11/2518* (2013.01); *G01N 21/954* (2013.01); *G02B 23/243* (2013.01); *G02B 23/2461* (2013.01); *G01N 2021/9544* (2013.01); *G02B 5/005* (2013.01)

(58) Field of Classification Search
  USPC .................................. 356/241.1, 237.2–237.6
  See application file for complete search history.

(56) References Cited

U.S. PATENT DOCUMENTS

| | | | |
|---|---|---|---|
| 5,150,234 A | 9/1992 | Takahashi et al. | |
| 5,293,872 A * | 3/1994 | Alfano | A61B 5/0071 |
| | | | 600/475 |
| 5,596,666 A * | 1/1997 | Miyano | A61B 1/07 |
| | | | 385/118 |
| 5,669,871 A * | 9/1997 | Sakiyama | A61B 5/1076 |
| | | | 348/135 |
| 5,713,364 A * | 2/1998 | DeBaryshe | A61B 1/00059 |
| | | | 250/461.2 |
| 6,040,910 A | 3/2000 | Wu et al. | |
| 6,564,088 B1 * | 5/2003 | Soller | A61B 5/0075 |
| | | | 600/478 |
| 6,570,657 B1 * | 5/2003 | Hoppe | G01N 21/553 |
| | | | 356/445 |
| 7,330,305 B2 * | 2/2008 | Harris | G02B 21/0076 |
| | | | 356/303 |
| 7,570,988 B2 * | 8/2009 | Ramanujam | A61B 5/0091 |
| | | | 356/303 |
| 8,040,527 B2 | 10/2011 | Kunz et al. | |
| 8,547,424 B2 * | 10/2013 | Ishii | A61B 1/00096 |
| | | | 348/68 |
| 9,069,181 B2 | 6/2015 | Harding et al. | |
| 2006/0042083 A1 | 3/2006 | Baker et al. | |
| 2007/0035852 A1 | 2/2007 | Farr | |
| 2009/0001059 A1 | 1/2009 | Spallek et al. | |
| 2010/0008588 A1 * | 1/2010 | Feldkhun | G01B 11/2518 |
| | | | 382/206 |
| 2010/0296104 A1 | 11/2010 | Abramovich et al. | |
| 2010/0297083 A1 | 11/2010 | Bresler et al. | |
| 2011/0297083 A1 | 12/2011 | Bartels et al. | |
| 2013/0083386 A1 * | 4/2013 | Harding | G01N 21/21 |
| | | | 359/240 |

FOREIGN PATENT DOCUMENTS

| | | |
|---|---|---|
| DE | 102007029728 A1 | 1/2009 |
| DE | 102008002730 A1 | 12/2009 |
| DE | 102010016264 A1 | 10/2011 |
| DE | 102012109278 | 4/2013 |
| EP | 2310891 A1 | 4/2011 |
| JP | H06141329 | 5/1994 |
| JP | 2004080605 A | 3/2004 |
| JP | 2008158046 A | 7/2008 |
| JP | 2010102265 A | 5/2010 |
| WO | WO2011120688 A1 | 10/2011 |

OTHER PUBLICATIONS

Ballard, D.H. & Brown, C.M.; Computer Vision, Prentice-Hall, Englewood Cliffs, New Jersey, 1982.
Forsyth, D. & Zisserman, A.; Reflections on Shading; IEEE Transactions on Pattern Analysis and Machine Intelligence, vol. 13, Iss. 7, pp. 671-679, 1991.
Reithmeier, et al.; Endoskopische 3D-Messtechnik (Endoscopic 3D metrology); DGAO Jahrestagung, Karlsruhe 2014, H5 (Abstract with English translation of abstract).
Heist, et al.; Array-Projektion aperiodischer Sinus-Muster zur Hochgeschwindigkeits-3DFormvermessung (Array projection periodic sinusoidal pattern for high speed 3D shape measurement); DGAO Jahrestagung, Karlsruhe 2014, A5 (Abstract with English translation of abstract).
Hofmann, et al.; 3D-Phasenmessung—ein hochentwickeltes Mess— und Bildgebungssystem (3D Phase Measurement—a sophisticated measurement and imaging system); DGZfP-Jahrestagung 2011 (English translation of summary).
Jähne, Bernd; Digital Image Processing, (5th Edition); Springer, Berlin Heidelberg, 2002.
Pennington, et al, Miniaturized 3-D surface profilometer using a fiber optic coupler, Optics & Laser Technology 33(2001) 313-320.
Li et al, High-speed 3D shape measurement with fiber interference, (2014). Mechanical Engineering Conference Presentations, Papers, and Proceedings. Paper 70.
Korczewski, Analysing the potential for application of the phase shift method in endoscopic examination of marine engines, Polish Maritime Research 1(77) 2013, vol. 20, pp. 23-30.
European Search Report dated Jul. 20, 2016 from counterpart EP App No. 16151830.3.
German Search Report dated Jan. 29, 2015 for counterpart German Application No. DE 10 2015 201 561.0.

* cited by examiner

MEASURING HEAD OF AN ENDOSCOPIC DEVICE AND PROCESS FOR INSPECTING AND MEASURING AN OBJECT

REFERENCE TO RELATED APPLICATION

This application claims priority to German Patent Application No. 10 2015 201 561.0 filed on Jan. 29, 2015, the entirety of which is incorporated by reference herein.

BACKGROUND

This invention relates to a measuring head of an endoscopic device and a method for inspection and measurement of an object using an endoscope with a measuring head of this type.

The use of endoscopes for optical inspections in the technical and medical fields is known. This requires the use of different lenses in the endoscopes, depending on the required resolution and depth of field.

SUMMARY

An object underlying the present invention is to provide a measuring head of an endoscopic device that can be used for different measurement tasks and resolution requirements. Furthermore, a method for inspection and measurement of an object is to be provided that can perform various measurement tasks using a measuring head of this type.

It is a particular object of the present invention to provide solution to the above problems by a measuring head of an endoscopic device having the features as described herein and a method for inspection and measurement of an object having the features as described herein.

Accordingly, the solution in accordance with the invention provides a measuring head of an endoscopic device having an optical projection unit (projection optics) for illuminating an object to be examined with light, and an optical measurement unit (measurement optics) for recording the light reflected or diffused from the object to be examined. In accordance with the invention, the optical measurement unit has an aperture diaphragm of which the aperture is settable.

The settability of the aperture makes it possible to perform different measurement tasks with no change in the lenses of projection optics and measurement optics. It is thus possible, by setting a small aperture for the aperture diaphragm, to obtain larger image fields in a greater depth of field, so that an inspection function can be provided where a first overview is obtained of the optical inspection to be performed. By setting a larger aperture, however, the resolution of the imaging is increased with a smaller depth of field, so that a measurement function can be performed. It can for example be provided that firstly an overview of a measurement to be performed is obtained using a small aperture, and then the measurement is performed with a large aperture setting with high resolution capacity in an identified area.

The invention provides a flexibly usable measuring head which can be used for various measurement tasks without the need to use different lenses.

According to an embodiment of the invention, it is provided that the aperture diaphragm is formed by a colour filter, with the aperture of the colour filter depending on the light wavelength. To obtain a colour filter of this type, it can be provided that the colour filter has at least two concentric zones with differing transmission spectra for light. For example, an inner concentric zone is permeable to white light, while an outer concentric zone arranged around the inner zone is permeable only to light of a defined wavelength, for example blue light, or to light of a wavelength range. The aperture of the aperture diaphragm can be set in steps here. If there are more than two concentric zones, step-by-step setting is also possible in more than two states.

It is pointed out that the aperture diaphragm can be arranged at various points inside the measurement optics. Typical locations for arrangement of the aperture diaphragm in the measurement optics are the locations of the entrance pupil, of the exit pupil and of an aperture diaphragm of the lens.

Together with the settability of the colour filter aperture depending on the light wavelength, it is necessary that the endoscopic device containing the measuring head in accordance with the invention is intended and suitable for providing light of different wavelengths for the measurement optics. To do so, it can for example be provided that in optical waveguides that pass light to the measurement optics, light of different spectra, for example blue light or red light, can be optionally injected. In another example, illumination for the inspection function uses white light through optical fibers in the measuring head, while for the measurement function light of a defined wavelength or of a defined wavelength range is used, for example red light. It can be provided here that the light for the measurement function is provided by other illumination optics, i.e. different illumination optics are used for the inspection function and for the measurement function.

In a further embodiment of the invention, it is provided that the colour filter works continuously, so that a continuous aperture setting can be achieved by a filter gradient.

The light paths in the measurement optics pass, for the colour filter apertures that differ depending on the light wavelength, through a hole, a ring or another opening in the colour filter.

The lenses used for the projection optics and the measurement optics can consist in a manner known per se of classic lens elements, aspheres and/or diffractive elements.

According to an alternative embodiment of the invention, it is provided that the aperture diaphragm is formed by a polarization filter, where the aperture of the polarization filter depends on the polarization of the light. To do so, it can for example be provided that the polarization filter has at least two concentric zones with different polarization directions. This embodiment of the invention is thus based on the idea of providing different numerical apertures using a polarization filter which is permeable for different polarizations in different areas. For example, it can be provided that the center of the filter is permeable for all polarization directions, while a concentric zone arranged around the center is permeable only to light of one polarization direction. In an alternative embodiment, it can be provided that the center is permeable only to light of a first polarization direction, while a concentric zone arranged around the center is permeable only to light of a second polarization direction.

This embodiment of the invention provides that different apertures are obtained by a separation of the light paths through filter zones of different polarization directions. The different apertures can in turn be obtained by a hole, a ring or another opening in the polarization filter.

For the settability of the aperture using the polarization of the light too, it is necessary that the endoscopic device in which the measuring head in accordance with the invention is used is intended and designed to provide light of different polarization directions. To do so, it can for example be provided that light of differing polarization directions can be injected into an optical waveguide that supplies light to the measurement optics.

According to the invention, it is provided that the aperture diaphragm is designed settable in respect of its aperture. To do so, it can be provided in further exemplary embodiments that the aperture diaphragm is mechanically settable, e.g. has motor-powered or manually controlled adjusting elements or other switchable elements permitting settability of the aperture.

In a further aspect of the invention, it is provided that the projection optics include means for projecting a pattern such as a one-dimensional or two-dimensional grating onto the object to be examined. The pattern projected onto the object to be examined is then recorded by the measurement optics and imaged onto a sensor system that can evaluate the pattern in respect of three-dimensional (3D) information. In this way, a 3D measurement of objects or defects is possible as part of a high-resolution measurement with large aperture.

This type of 3D measurement can be performed using triangulation methods known per se. Due to the topology of the object to be measured, distortions of the pattern on the object to be examined are here evaluated in respect of the 3D information provided by these distortions. According to this embodiment of the invention, an optical measurement unit (measurement optics) with variable aperture is thus combined with an optical projection unit (projection optics) that performs a structural projection onto the object to be examined, so that a 3D measurement of objects or structures is made possible in particular by triangulation methods. A large aperture is set in the measurement optics for high-resolution measurements in the µm range, and a small aperture is set for an overview inspection.

It can be provided here that other illumination means are used for the inspection function than for the measurement function. Also, it can be provided that a grating is projected in the case of the measurement function onto the object which in the case of the inspection function cannot be imaged or can be additionally imaged.

This embodiment makes it possible to perform during technical and medical endoscopy, besides general inspection by imaging methods, 3D measurements of the dimensions of selected objects too, with the height, width and depth of technical defects or medical objects being measured in particular. With high-precision non-contacting 3D measurement methods, technical maintenance inspections of turbines and vehicles, for example, can be made substantially more efficient. By means of the inspection function using a small aperture, the defects are roughly localized in order to measure them afterwards in the measurement function of the same lens using a large aperture. As explained, the evaluation is based on a triangulation evaluation of a pattern projected onto the object to be examined and which can be a one-dimensional or two-dimensional linear system, for example a grating.

The measuring head provided according to this embodiment of the invention is also suitable for three-dimensional measuring of structures in the µm range, using for this purpose optics with high resolution capacity and correspondingly large aperture. This is not possible with 3D measurement methods previously used in endoscopy, in particular the so-called phase method, as is known from US 2010/0296104.

According to an embodiment, the stated means, which project a pattern onto the object to be examined, have a transmission grating. This can have several different grating constants in different grating areas. Due to the different grating constants, different frequencies can be optionally resolved, depending on which grating area of the transmission grating is imaged onto the object. To that extent, the grating is projected by the movement of the measuring head onto the object.

A further embodiment provides that the means projecting a pattern onto the object to be examined include at least two monomode optical waveguides, of which the coherent lights interfere with one another while forming a grating, where the space between the optical waveguides is settable in order to set the grating constants. Alternatively or additionally, the grating constant can also be set by changing the wavelength of the used light with a fixed distance of the optical waveguides from one another. This embodiment of the invention permits in simple manner, by exploitation of the physical processes of diffraction and interference, creation of a grating with settable grating constant.

If the phase relationship of the lights of the two monomode fibers relative to one another is set in a controlled manner, the created grating can be moved vertically to the lines, without mechanically moved parts, making scanning functions possible.

A further embodiment of the invention provides that the optical axes of the projection optics and measurement optics are at an angle, i.e. the projection optics and the measurement optics are inclined relative to one another. This is particularly useful for triangulation measurements with evaluation of a pattern projected onto the object to be examined, since it is necessary in triangulation measurements to provide an oblique arrangement or an angle between the projection optics and the measurement optics or the respective optical axes.

An embodiment of the invention provides for the projection optics to be designed such that off-centered imaging is made possible. To do so, it can for example be provided that the illumination fiber that injects light into the projection optics does not inject light on the optical axis of the projection optics, but off-centered, meaning parallel to this optical axis. This permits a more even illumination in the overlap area of the measurement and projection optics. It can be provided here that the means projecting a pattern onto the object to be examined (for example a transmission grating) are also arranged off-centered relative to the optical axis of the projection optics. This makes possible an additional inclination, or a larger triangulation angle for a triangulation measurement.

According to an embodiment of the invention, it is provided that the measuring head furthermore has a sensor intended and designed to record the image generated by the measurement optics and if necessary further evaluate it. The sensor generates here a monitor image and permits digital image processing. It can however also be provided that the image provided by the projection optics e.g. by means of an image guide fiber that assigns a single optical fiber to each pixel dot, is extracted from the measuring head and the endoscope and the sensor for recording and evaluation of the light recorded by the measurement optics is arranged outside the measuring head and/or the endoscope. This ensures additional flexibility in the arrangement of the sensor.

It is pointed out that the projection optics can be designed such that in all settings of the aperture diaphragm there is only one optical unit that provides light and images onto the object. It can be provided here, as explained, that light of different wavelengths or polarization planes is injected into this single optical unit in order to obtain different apertures.

It is however also within the scope of the present invention that the projection optics have two optical units which are each used separately for the projection function and the measurement function. Hence, an embodiment of the invention provides that the projection optics have a first illumination unit and a second illumination unit, said first illumination unit being designed and intended to provide light when the aperture diaphragm adopts a first aperture, and said second illumination unit being designed and intended to provide light when the aperture diaphragm adopts a second aperture. The first illumination unit includes for example an optical waveguide and an imaging unit and where necessary additionally a condenser and a grating. It is for example used for the measurement function. The second illumination unit includes for example an optical fiber bundle, and is for example used for the inspection function.

The invention also provides a method for inspection and measurement of an object. This method is performed by the use of an endoscope with a measuring head designed as described herein. Here, a smaller aperture is set for performance of an inspection measurement with low resolution but greater depth of field, and a larger aperture for performance of a measurement function with higher resolution, but less depth of field.

An embodiment of the method provides that when the larger aperture is adopted, light of a first illumination unit is used for object illumination, and when a smaller aperture is adopted, light of a second illumination unit is used for object illumination. It can be provided here that when the smaller aperture is adopted, optical fiber bundles are used for object illumination.

According to a further embodiment, when the larger aperture is used, a pattern, for example a grating, is projected onto the object to be examined.

BRIEF DESCRIPTION OF THE DRAWINGS

The present invention is more fully described in the following with reference to the figures of the accompanying drawing showing several exemplary embodiments.

DETAILED DESCRIPTION

Figure 1:
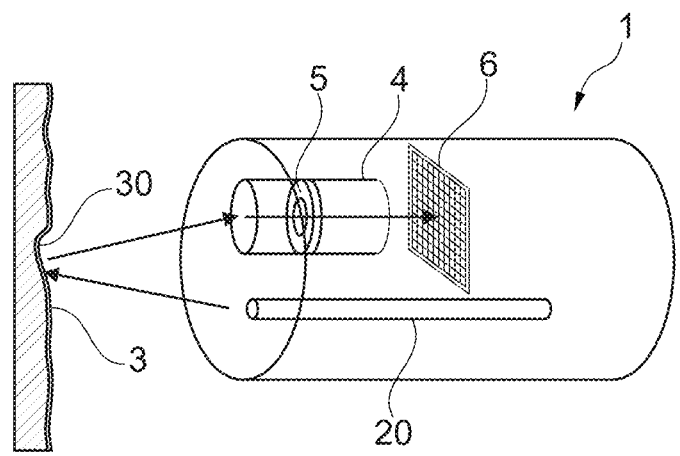
FIG. 1 schematically shows a first exemplary embodiment of a measuring head having an optical projection unit (projection optics), an optical measurement unit (measurement optics) and a settable aperture diaphragm.

FIG. 1 shows a first exemplary embodiment of a measuring head 1 of an endoscopic device having an optical measurement unit (measurement optics) with settable aperture. The measuring head 1 includes an optical projection unit (projection optics) 20, an optical measurement unit (measurement optics) 4 with an integrated aperture diaphragm 5 and a sensor 6.

The projection optics 20 are formed in the exemplary embodiment shown by a single optical waveguide that emits light onto an object 3 to be examined, which for example has a defect 30. The light emitted by the projection optics 20 is reflected and diffused from the object 3 to be examined and is recorded by the measurement optics 4. The measurement optics 4 image the surface to be examined of the object 3 to be examined onto the sensor 6. The sensor generates a monitor image that permits digital image processing and that can be further processed.

It is pointed out that the projection optics 20 consist only in the simplest case of a single optical waveguide. As is detailed below, the projection optics can also consist for example of a lens system having classic lens elements, aspheres and/or diffractive elements, or of several optical waveguides.

The aperture diaphragm 5 integrated into the measurement optics 4 is settable in respect of its aperture. The settability is achieved for example in that the aperture diaphragm is formed by a colour filter or by a polarization filter, where the aperture of the filter depends on the light wavelength or the polarization of the light.

Figure 2A:
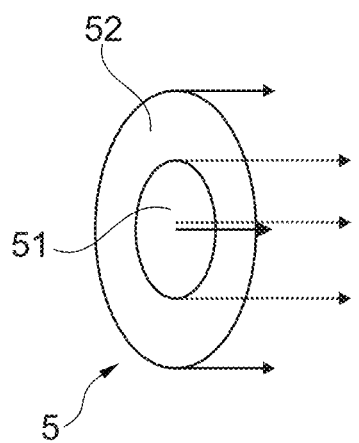
FIG. 2A shows a first exemplary embodiment of a colour filter settable in respect of the aperture.
Figure 2B:
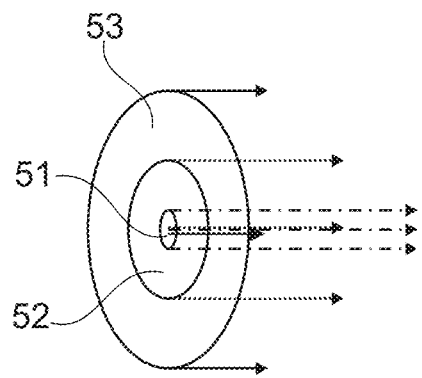
FIG. 2B shows a second exemplary embodiment of a colour filter settable in respect of the aperture.

FIGS. 2A, 2B show two exemplary embodiments for aperture diaphragms formed by a colour filter. In FIG. 2A a central filter zone 51 is permeable to visible light of all wavelengths. In an outer area 52 arranged concentrically to it, the colour filter is however only permeable to the spectrum of one of the colour groups of the sensor, for example to blue light. If for example blue light is injected, both areas 51, 52 are permeable to the blue light, so that a large aperture is obtained. If however red light is injected, it can only pass through the central filter zone 51, so that a small aperture is obtained. Depending on the wavelength of the light used, two different apertures can thus be automatically provided.

FIG. 2B shows an exemplary embodiment for a colour filter that can adopt three different numerical apertures, depending on whether light can only pass through the central filter zone 51 or additionally through the further concentric zones 52, 53. For example, the central filter zone 51 is permeable to light of all wavelengths. The adjoining concentric filter zone 52 is permeable to light of a first wavelength or a first wavelength range and the second concentric filter zone 53 to light of a second wavelength or a second wavelength range.

Figure 3:
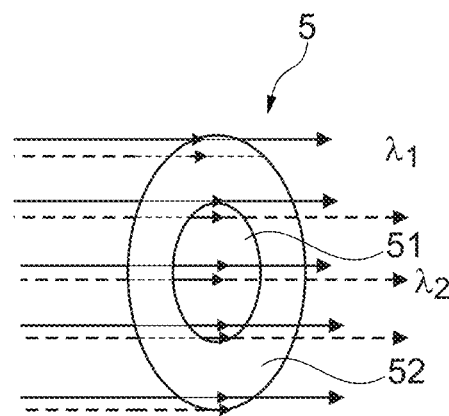
FIG. 3 shows a further representation of the colour filter of FIG. 2A, illustrating the transmitted wavelengths.
Figure 4:
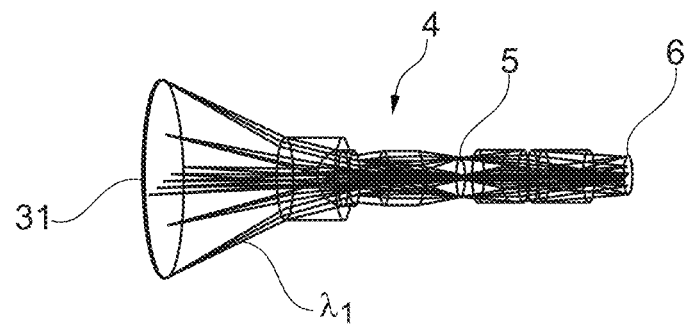
FIG. 4 shows an exemplary embodiment of the measurement optics using light of a first wavelength and with large aperture.
Figure 5:
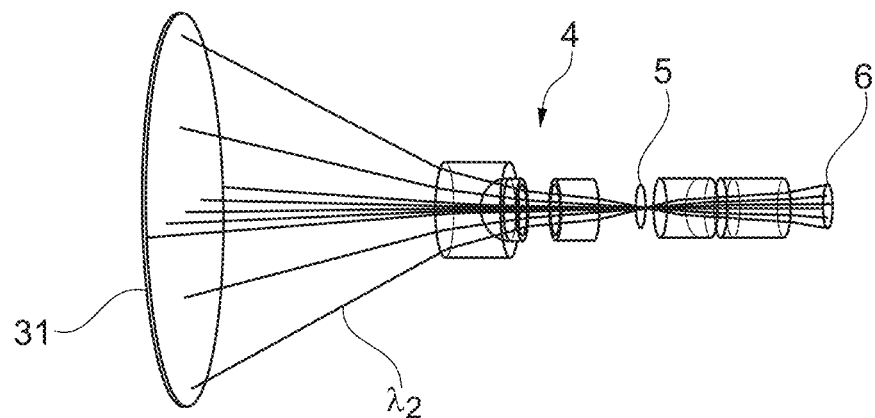
FIG. 5 shows the measurement optics of FIG. 4 using light of a second wavelength and with small aperture.

FIGS. 3 to 5 further make clear the mode of operation of a colour filter acting as an aperture diaphragm according to FIG. 2A. With the colour filter 5 of FIG. 3, the central filter zone 51 is permeable to white light (and hence to blue light of the wavelength $\lambda_1$ or of the wavelength range $\Delta\lambda_1$ and to red light of the wavelength $\lambda_2$ or of the wavelength range $\Delta\lambda_2$). The filter zone 52 concentrically adjoining it is only permeable to blue light of the wavelength $\lambda_1$ or of the wavelength range $\Delta\lambda_1$.

If blue light of the wavelength $\lambda_1$ is injected via the projection optics 20, the result is a large aperture, since both zones 51, 52 transmit the blue light of the wavelength $\lambda_1$. The large aperture corresponds to a high resolution capacity and a small depth of field. If red light is injected through the projection optics 20, the outer filter area 52 blocks this red light, so that it can pass only through the central filter zone 51. Accordingly, a small aperture is now obtained which corresponds to a greater depth of field and a lower resolution capacity. This is shown in FIGS. 4 and 5 showing the measurement optics 4 for the wavelengths $\lambda_1$ and $\lambda_2$.

Figure 6:
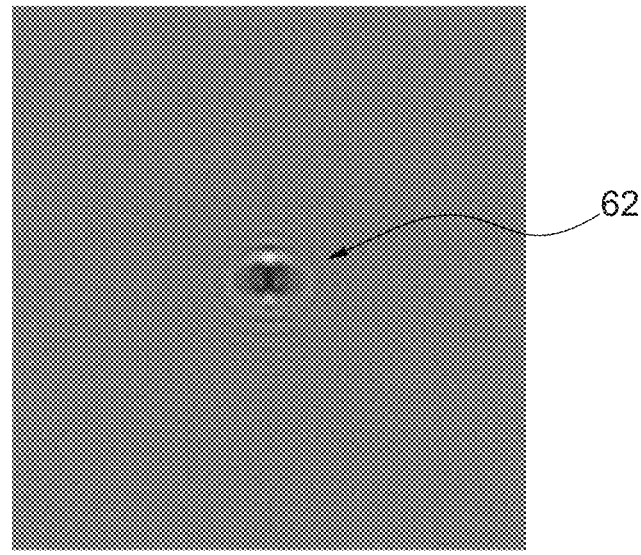
FIG. 6 shows the simulation of imaging a gap, when the measurement optics perform an inspection function with small aperture.
Figure 7:
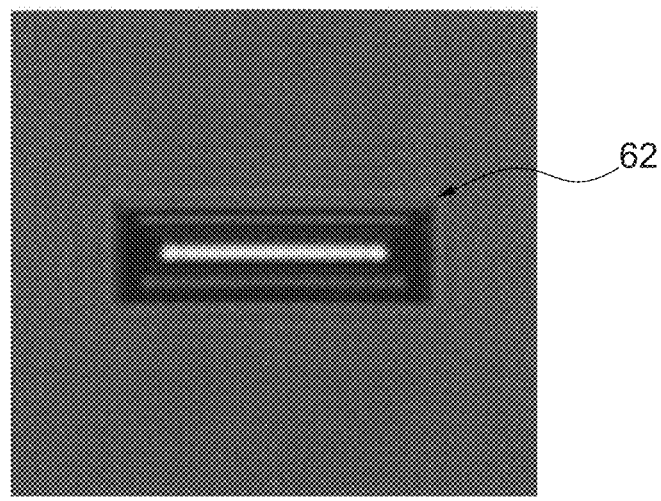
FIG. 7 shows the simulation of imaging a gap, when the measurement optics perform a measurement function with large aperture.

FIG. 6 illustrates a defect 62 (e.g. a trough) of 50 μm×150 μm in size when a small aperture is used in the aperture diaphragm 5. For example, the numerical aperture is 0.02. The defect 62 is discernible due to the small aperture and the correspondingly low resolution, but not resolved. FIG. 7 shows the same defect 62 using the large aperture of the aperture diaphragm 5. The defect 62 is now resolved due to the higher resolution capacity with the large aperture and can be measured.

Figure 8A:
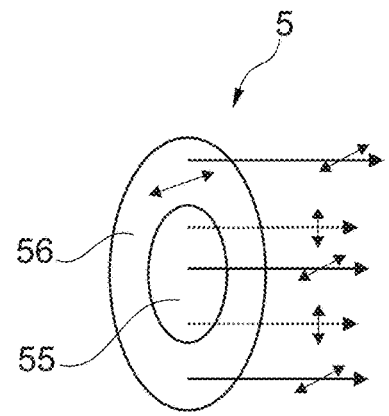
FIG. 8A shows a first exemplary embodiment of a polarization filter settable in respect of the aperture.
Figure 8B:
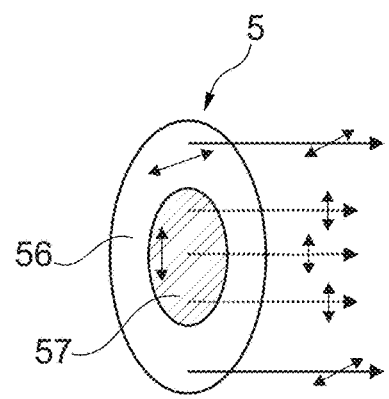
FIG. 8B shows a second exemplary embodiment of a polarization filter settable in respect of the aperture.

FIGS. 8A, 8B show two exemplary embodiments for aperture diaphragms corresponding to the aperture diaphragm 5 in FIG. 1 and formed by polarization filters.

FIG. 8A shows a first exemplary embodiment of a polarization filter with two numerical apertures. A central filter zone 55 is permeable for all polarization directions, while the ring 56 concentrically extending around it is transparent only to light polarized in the x-direction (vertical to the blade plane).

When light polarized in the x-direction is emitted via the projection optics 20 and is recorded after reflection or diffusion from the object 3 to be examined by the projection optics 4, then the polarization filter 5 is permeable in both zones 55, 56, since the center 55 is permeable for both polarization directions and the outer ring 56 for polarization in the x-direction. If however light polarized in the y-direction is injected, only the central filter zone 55 is permeable, since the outer filter zone 56 blocks light polarized in the y-direction. Accordingly, the result is a large numerical aperture for light polarized in the x-direction and a small numerical aperture for light polarized in the y-direction.

The result is identical representations to those in FIGS. 4 and 5, with the aperture of the aperture diaphragm 5, unlike in FIGS. 4 and 5, depending not on the wavelength, but on the polarization direction. However, the same light paths result that are also shown in FIGS. 4 and 5.

FIG. 8B shows a further exemplary embodiment of a polarization filter 5. In this embodiment, the central filter zone 57 is only permeable to that proportion of the light polarized in the y-direction (parallel to the blade plane), while the outer filter zone 56 is permeable only to that proportion of the light polarized in the x-direction. The result is that the polarization filter is permeable to light polarized in the x-direction only in its ring area 56 and is permeable to light polarized in the y-direction only in its central area 57. A filter settable in its aperture is again provided.

Figure 9A:
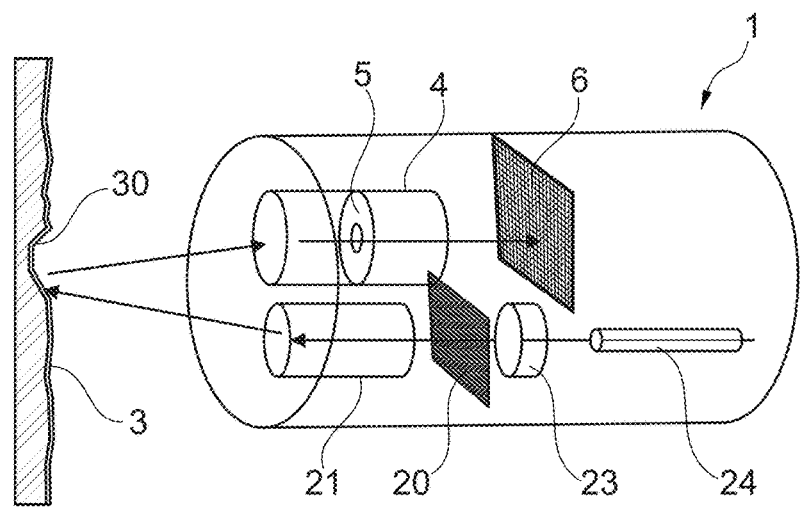
FIG. 9A schematically shows a second exemplary embodiment of a measuring head having an optical projection unit (projection optics), an optical measurement unit (measurement optics) and a settable aperture diaphragm.

FIG. 9A shows a further exemplary embodiment of a measuring head in accordance with the invention. This measuring head differs from the measuring head in FIG. 1 in particular in the embodiment of the projection optics, the latter including an optical waveguide 24 that supplies light, a condenser 23, a grating 22 and, as actual projection optics, the grating imaging optics 21, which images the grating 22 onto the object 3 to be examined (which has for example a defect 30). The reflected image is recorded by the optical unit (optics) 4, which in turn—just as described in relation to FIG. 1—has a variable aperture diaphragm 5, and is imaged onto a sensor 6.

The measurement optics 4 can thus adopt different apertures by means of a settable aperture diaphragm. To that extent, reference is made to the statements on FIGS. 1 to 8B. The optical measurement unit (measurement optics) 4 is thus able to perform both an inspection function and a measurement function. The measurement unit 4 images the surface to be examined onto the sensor 6. The sensor 6 generates a monitor image and permits digital image processing. It can be provided here that the light is first projected onto an image guide fiber and from there is passed to a sensor arranged outside the endoscope.

The optical projection unit is intended for projecting the pattern provided by the grating 22 onto the surface of the object 3 to be examined. The pattern, e.g. a grating, is here illuminated by the illumination optics consisting of the condenser 23 and the optical waveguide 24. The lens of the measurement optics 4 is designed such that it is able to image the pattern deformed by the topography in resolved form onto the sensor 6. Defects in the x and y dimensions can then be measured by image processing. By the additional application of triangulation methods, the depth z at location x, y can be determined from the knowledge of the incidence and observation angle and from the deformation of the line. This permits a complete reconstruction of the surface including the defects.

In FIG. 9A it is provided that the optical projection unit (including the optical waveguide 24, the condenser 23, the grating 22 and the grating imaging optics 21) both provides light and images it onto the object 3 when the aperture diaphragm 5 adopts a small aperture and hence performs an inspection function, and when the aperture diaphragm 5 adopts a large aperture and hence performs a measurement function. This is however by no means necessarily the case.

Figure 9B:
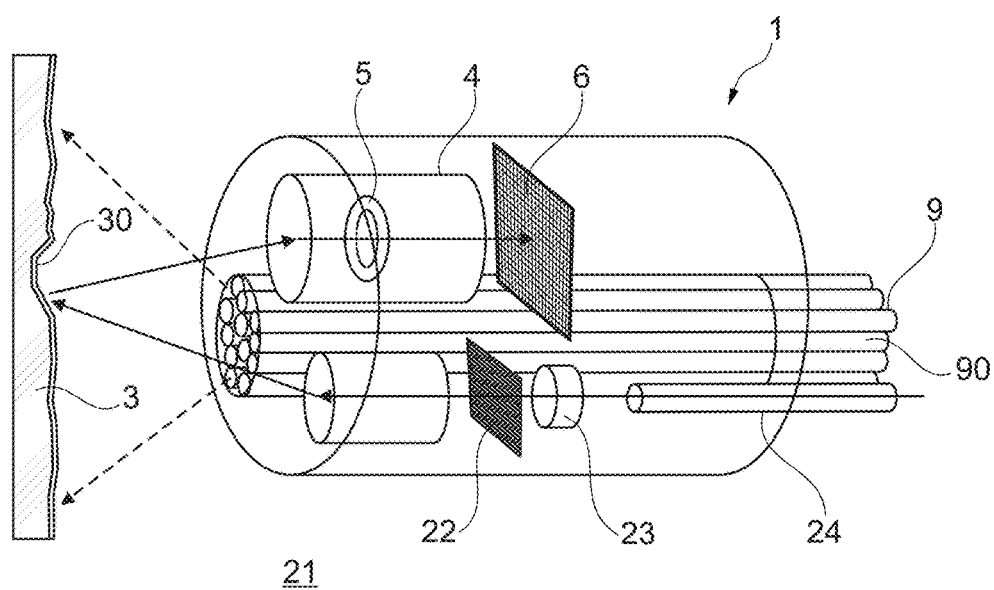
FIG. 9B shows a variant of the exemplary embodiment of FIG. 9A, where a general object illumination is additionally provided.

FIG. 9B thus shows a variant of the exemplary embodiment in FIG. 9A in which the projection optics include an additional illumination unit 9 in the form of an optical fiber bundle 90. Alternatively, the additional illumination unit 9 could for example be provided by an LED or an LED with optical fiber bundle. The additional illumination unit 9 provides object illumination when the measuring head 1 is used for an inspection function. When the measuring head 1 is used for a measurement function, however, the projection unit is used with optical waveguide 24, condenser 23, grating 22 and grating imaging optics 21.

Figure 10:
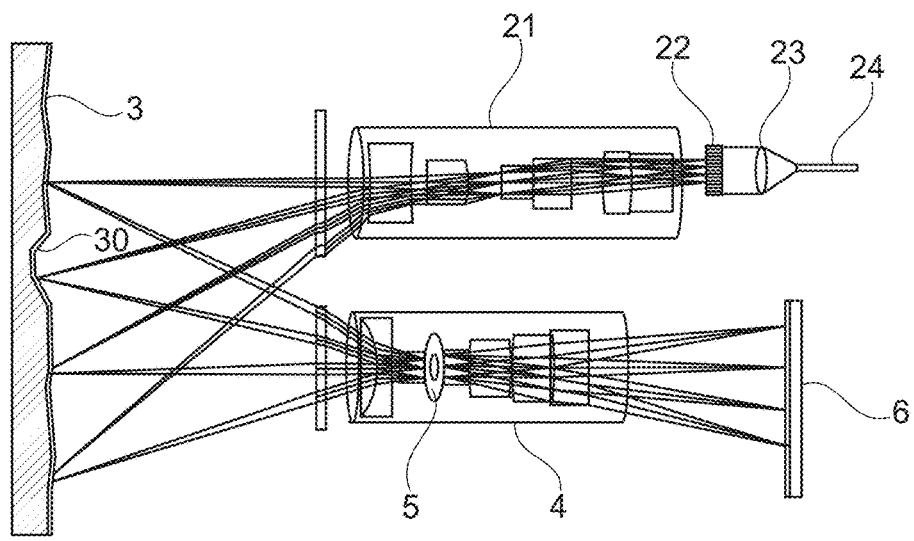
FIG. 10 shows a measuring head corresponding to the measuring head of FIG. 9A, where the light paths are illustrated with an off-centered injection of light into the projection optics.

FIG. 10 shows in more detail the mode of operation of a measuring system according to FIG. 9. It is provided here that the light injection from the optical fiber 24 via the condenser 23 and the grating 22 into the grating imaging optics 21 is off-centered, i.e. not symmetrical to the optical axis of the grating imaging optics 21, but offset parallel to it. This is shown schematically in FIG. 10. The result of this is that the pattern projected by the projection optics obliquely onto the surface of the object 3 to be examined impinges at a more oblique angle and hence the triangulation angle required for triangulation measurement is increased. An additional off-centering of the optical fiber such that at least one first order of diffraction passes through the grating imaging optics without shadowing permits homogenization of the resolution capacity in the measurement window on the object.

The pattern projected obliquely by the projection optics 21, 22, 23, 24 onto the surface is obliquely detected by the measurement optics 4. In this way, the angle needed for a triangulation is obtained as the sum of both angles. The angle setting is, as already mentioned, achieved by off-centered imaging of the projection optics. It can be additionally or alternatively achieved by additional optical elements such as mirrors, prisms, diffraction gratings and diffractive elements. It can also be provided that the measurement optics 4 and the projection optics are arranged at an angle to one another, i.e. inclined to one another, with their optical axes forming an angle (not shown separately).

Setting of the aperture by the aperture diaphragm 5 is achieved for example—as described in relation to FIGS. 1 to 8B—by providing the aperture diaphragm as a colour filter or as a polarization filter. It can also be provided that the settability of the aperture diaphragm is achieved in a different manner, such as mechanically, for example by motor-powered adjusting elements or electrochromic or thermochromic elements. Aperture diaphragms on the basis of polarization filters can also be designed electrically switchable by the use of liquid crystals. The aperture diaphragm 5 settable in its aperture is also shown schematically in FIG. 10. In respect of the different light paths resulting from the different aperture for performance on the one hand of an inspection function and on the other hand for performance of a measurement function, reference is again made to FIGS. 4 and 5, which also apply for the exemplary embodiment in FIGS. 9 and 10.

Figure 15:
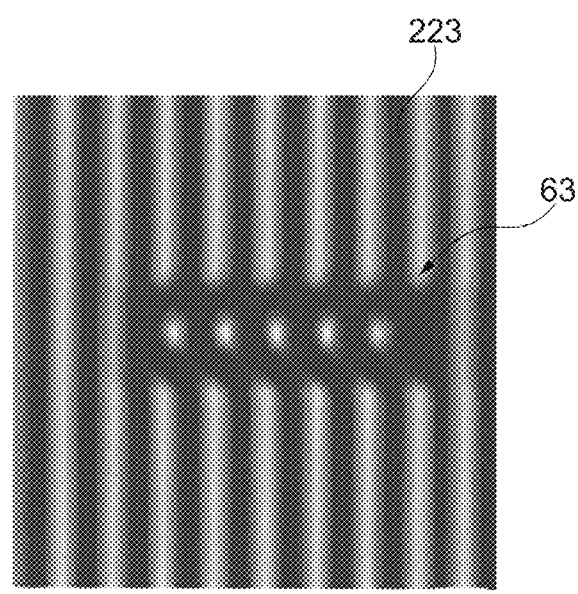
FIG. 15 shows the simulation of an image of a grating deformed by a defect and projected onto the object to be examined.

FIG. 15 shows the simulation of the image of a grating onto the surface of an object to be examined, where the grating has a pitch of 20 µm and a gap width of 7 µm. The grating is projected onto a surface which has a defect 63 in the form of a scratch having a width of 50 µm and a depth of 20 µm. Accordingly, in FIG. 15 the grating lines are deformed in the area of the defect 63. The optical measurement unit 4 has in the exemplary embodiment considered an aperture of $NA_m=0.1$ with defocusing of 25 µm and a wavelength of 633 nm. In the measurement mode (large aperture), the image with the deformed grating lines can be imaged by the projection optics 4 in resolved form onto the sensor 6, so that the three-dimensional shape of the defect 63 can be determined from the deformation of the grating lines by means of triangulation methods.

Figure 11:
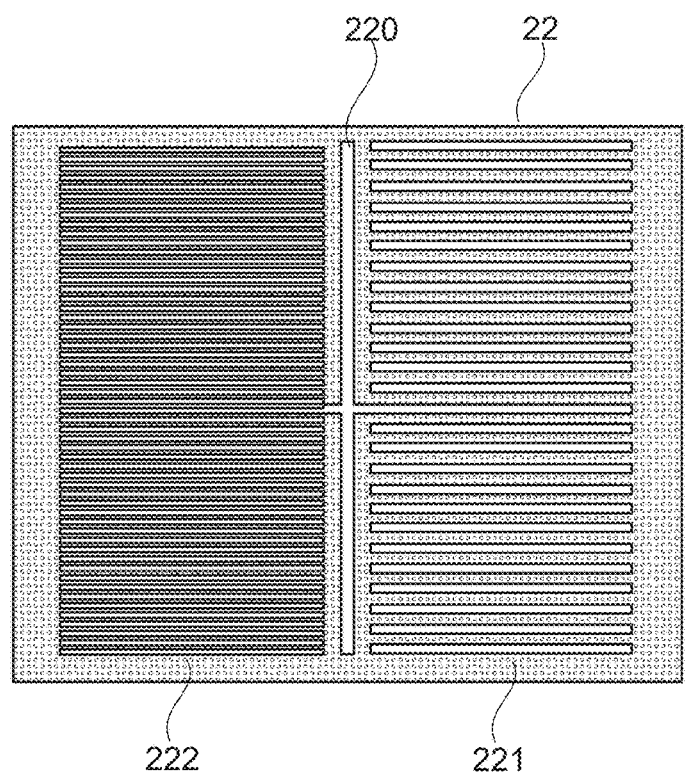
FIG. 11 shows an exemplary embodiment of a transmission filter used with the measuring head of FIGS. 9A, 9B or FIG. 10.

In FIGS. 9A, 9B and 10, the grating is provided as a transmission grating designed for example as a glass plate, onto which for example grating structures of chromium are applied. An example of a transmission grating of this type is shown in FIG. 11. The transmission grating 22 images here different grating constants in the areas 221, 222. Additionally, the grating can include a central element, for example a cross 220. The different grating constants can be used depending on the resolution or aperture setting and serve for adjustment, image processing and increasing the clarity of the reconstruction.

Figure 12:
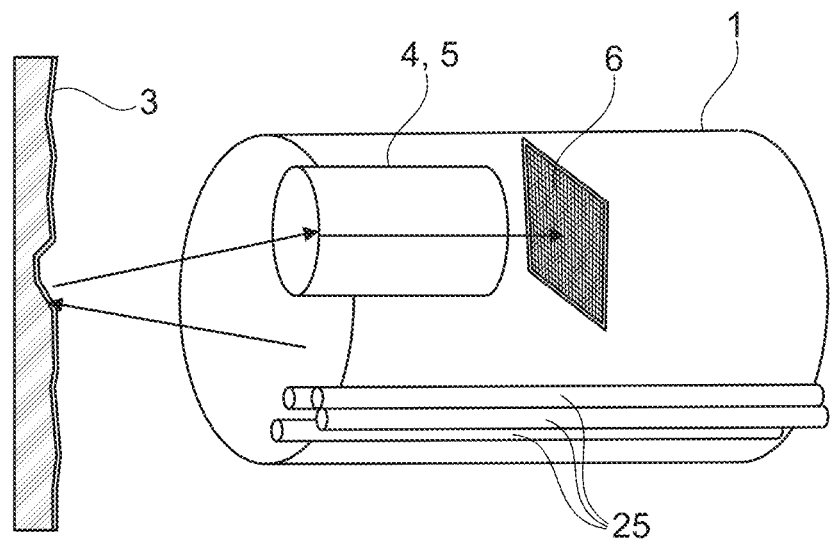
FIG. 12 schematically shows a third exemplary embodiment of a measuring head having an optical projection unit (projection optics) and an optical measurement unit (measurement optics) with settable aperture, with the projection optics being obtained by a plurality of optical waveguides.
Figure 13:
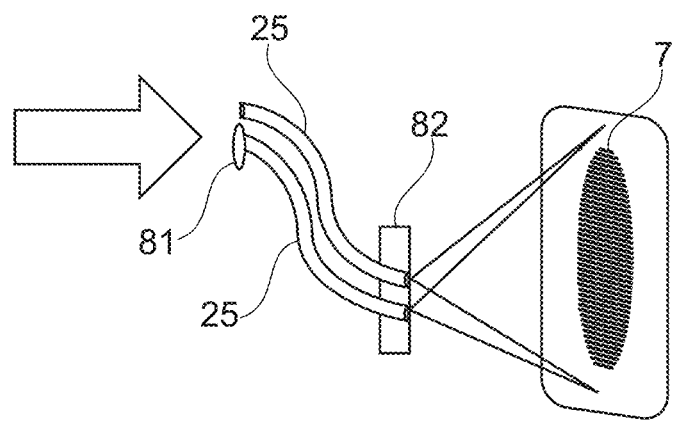
FIG. 13 schematically shows the functional principle of the use of two monomode optical waveguides for generating a grating.

FIGS. 12 and 13 show an alternative exemplary embodiment for obtaining a grating. The exemplary embodiment in FIG. 12 shows a measuring head 1 in which the projection optics 21, 22, 23, 24 of FIGS. 9 and 10 are replaced by a plurality of parallel-arranged monomode optical waveguides 25. These monomode optical waveguides are arranged such that the lights emitted by them interfere with one another, with a grating being generated. This is shown schematically in FIG. 13. Light from a laser is injected into two monomode fibers 25, where injection into one of the monomode fibers uses a λ/2 wafer 81 for adjusting the polarization of the fibers. The λ/2 wafer 81 can be dispensed with if polarization-maintaining monomode fibers are used. The two monomode fibers 25 are held with a defined spacing in a mounting 82. Due to interference matching the interference at a double gap, a grating 7 is created. The advantage of this embodiment is that the grating spacing is set in simple manner either by the distance between the two monomode fibers 25 in the area of the mounting 82 or by variation of the wavelength used, permitting an improvement of the triangulation measurement.

In all exemplary embodiments and hence also in the exemplary embodiment in FIGS. 12 and 13, it can be provided that the optical projection unit has a separate illumination unit (corresponding to the illumination unit 9 of FIG. 9B) by means of which the object 3 is illuminated during performance of the inspection function.

Figure 14:
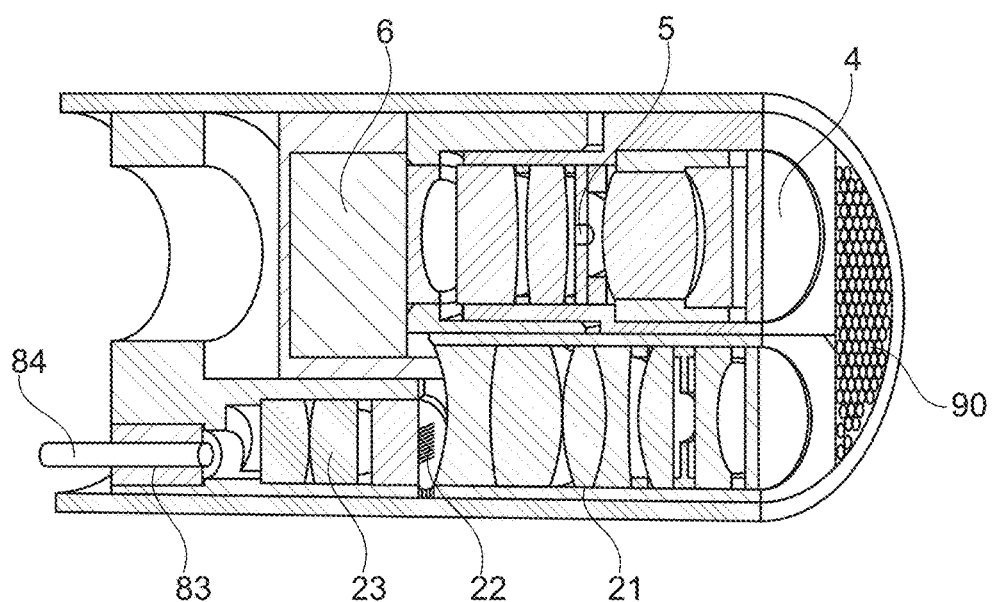
FIG. 14 shows a fourth exemplary embodiment of a measuring head having an optical projection unit (projection optics), an optical measurement unit (measurement optics), a settable aperture diaphragm and a general object illumination.

FIG. 14 shows a further exemplary embodiment of a measuring head in accordance with the invention. This exemplary embodiment shows as examples lens systems which provide the projection optics 21, 22, 23 and the measurement optics 4. A mounting 83 is provided for holding an optical fiber 84 that supplies illumination light for imaging of the grating and for the measurement function. It can be clearly discerned that both the grating 22 is arranged off-center to the imaging optics 21 and the injection of light into the imaging optics 21 is off-center, i.e. offset to the optical axis of the imaging optics 21. The sensor is provided in a sensor assembly 6. An aperture diaphragm 5 with settable aperture is again provided, which is designed for example as a colour filter diaphragm or as a polarization filter diaphragm. The illumination for the inspection function is provided corresponding to FIG. 9B by an optical fiber bundle 90 which is shown schematically.

The invention in its design is not restricted to the above mentioned exemplary embodiments, which are only to be understood as examples. In particular, the invention is not limited to certain embodiments of projection optics, measurement optics or of an aperture diaphragm.

It is furthermore pointed out that the features of the individual exemplary embodiments described of the invention can be combined in various combinations with one another. Where areas are defined, they include all the values within these areas and all the sub-areas falling within an area.

What is claimed is:
1. A measuring head of an endoscopic device comprising:
an optical projection unit including a light source for illuminating an object to be examined with light, and an optical measurement unit including a light sensor for recording the light reflected or diffused from the object to be examined, wherein the optical measurement unit has an aperture diaphragm including a variable aperture;

an aperture setting unit selectively changing the variable aperture between:
- a first size of the variable aperture providing a lower resolution for inspecting the object;
- a second size of the variable aperture larger than the first size providing a higher resolution for measuring the object;

the optical projection unit including a pattern forming element for projecting a pattern onto the object; the pattern being imagable when the variable aperture changed to the second size providing the higher resolution for measuring the object and non-imagable when the variable aperture changed to the first size providing the lower resolution for inspecting the object.

2. The measuring head in accordance with claim 1, wherein the aperture setting unit includes a color filter forming the aperture diaphragm, with the variable aperture of the color filter depending on a wavelength of the light from the light source.

3. The measuring head in accordance with claim 2, wherein the color filter has at least two concentric zones with differing transmission spectra for light.

4. The measuring head in accordance with claim 1, wherein the aperture setting unit includes a polarization filter forming the aperture diaphragm, where the size of the variable aperture depends on a polarization of the light from the light source.

5. The measuring head in accordance with claim 4, wherein the polarization filter includes at least two concentric zones with different polarization directions.

6. The measuring head in accordance with claim 1, wherein the aperture setting unit sets the size of the aperture by at least one chosen from mechanically, electro-optically, electro-chromatically, thermo-chromatically and by switchable liquid crystals.

7. The measuring head in accordance with claim 1, wherein the pattern forming element includes a transmission grating.

8. The measuring head in accordance with claim 7, wherein the transmission grating has different grating constants in different grating areas.

9. The measuring head in accordance with claim 1, wherein the pattern forming element includes at least two monomode optical waveguides, lights of which interfere with one another while forming a grating, where a space between the optical waveguides is settable in order to set grating constants of the grating.

10. The measuring head in accordance with claim 1, wherein the measuring head further includes an image processing unit for evaluating distortions of a grating line on the object with respect to 3D information provided by the distortions.

11. The measuring head in accordance with claim 1, wherein the optical axes of the optical projection unit and the optical measurement unit are at a non-zero angle.

12. The measuring head in accordance with claim 1, wherein the optical projection unit is designed such that a centered imaging or an off-centered imaging is provided.

13. The measuring head in accordance with claim 1, wherein the aperture setting unit includes a first illumination unit of the optical projection unit and a second illumination unit of the optical projection unit, the first illumination unit being arranged and constructed to provide light such that the aperture diaphragm adopts the first size of the variable aperture, and the second illumination unit arranged and constructed to provide light such that the aperture diaphragm adopts the second size of the variable aperture.

14. The measuring head in accordance with claim 1, and further comprising a sensor for recording an image generated by the optical measurement unit.

15. A method for inspection and measurement of an object using an endoscope with a measuring head, comprising:
providing a measuring head of an endoscopic device comprising:
an optical projection unit including a light source for illuminating an object to be examined with light, and
an optical measurement unit including a light sensor for recording the light reflected or diffused from the object to be examined,
wherein the optical measurement unit has an aperture diaphragm including a variable aperture; the variable aperture being selectively settable between:
a first size of the variable aperture providing a lower resolution for inspecting the object;
a second size of the variable aperture larger than the first size providing a higher resolution for measuring the object;
the optical projection unit including a pattern forming element for projecting a pattern onto the object; the pattern being imagable when the variable aperture is set at the second size providing the higher resolution for measuring the object and non-imagable when the variable aperture is set at the first size providing the lower resolution for inspecting the object;
setting the first size of the variable aperture for performing an inspection of the object with low resolution;
setting the second size of the variable aperture for performing a measurement of the object with higher resolution.

16. The method in accordance with claim 15, and further comprising using the measuring head to measure defects in an aircraft engine.

17. The method in accordance with claim 15, wherein when the second size of the variable aperture is adopted, light of a first illumination unit is used for object illumination, and when the first size of the variable aperture is adopted, light of a second illumination unit is used for object illumination.

18. The method in accordance with claim 15, wherein when the first size of the variable aperture is adopted, using optical fiber bundles for object illumination.

19. The method in accordance with claim 15, wherein, when the second size of the variable aperture is used, projecting the pattern onto the object.

20. A measuring head of an endoscopic device comprising:
an optical projection unit including a light source for illuminating an object to be examined with light, and
an optical measurement unit including a light sensor for recording the light reflected or diffused from the object to be examined,
wherein the optical measurement unit has an aperture diaphragm including a variable aperture, the aperture diaphragm including:
a first zone including a first color filter being permeable to a first range of wavelength of light; the first zone establishing a first size of the variable aperture;
a second zone concentric to the first zone and positioned radially aligned with the first zone, the second zone including a color filter being permeable to a second range of wavelength of light different from the first range of wavelength of light; the second zone establishing a second size of the variable aperture different from the first size of the variable aperture;

wherein the aperture diaphragm is selectable between the first size of the variable aperture and the second size of the variable aperture depending on a wavelength of light transmitted by the optical projection unit;

wherein the first zone and second zone are simultaneously permeable to the light depending on the wavelength of the light transmitted by the optical projection unit.

21. A measuring head of an endoscopic device comprising:

an optical projection unit including a light source for illuminating an object to be examined with light, and an optical measurement unit including a light sensor for recording the light reflected or diffused from the object to be examined, wherein the optical measurement unit has an aperture diaphragm including a variable aperture, the aperture diaphragm including:

a first zone including a first polarization filter being permeable to a first polarization of light; the first zone establishing a first size of the variable aperture;

a second zone concentric to the first zone and positioned radially aligned with the first zone, the second zone including a second polarization filter being permeable to a second polarization of light different from the first polarization of light; the second zone establishing a second size of the variable aperture different from the first size of the variable aperture;

wherein the aperture diaphragm is selectable between the first size of the variable aperture and the second size of the variable aperture depending on a polarization of light transmitted by the optical projection unit;

wherein the first zone and second zone are simultaneously permeable to the light depending on the wavelength of the light transmitted by the optical projection unit.

22. A measuring head of an endoscopic device comprising:

an optical projection unit including a light source for illuminating an object to be examined with light, and an optical measurement unit including a light sensor for recording the light reflected or diffused from the object to be examined, wherein the optical measurement unit has an aperture diaphragm including a variable aperture;

the optical projection unit including a pattern forming element for projecting a pattern onto the object;

wherein the pattern forming element includes at least two monomode optical waveguides, lights of which interfere with one another while forming a grating, where a space between the optical waveguides is settable in order to set grating constants of the grating.

\* \* \* \* \*